(12) United States Patent
Yamada et al.

(10) Patent No.: US 8,609,438 B2
(45) Date of Patent: Dec. 17, 2013

(54) PROTEIN-IMMOBILIZED ELECTRODE AND METHOD OF MANUFACTURING THE SAME, AND FUNCTIONAL ELEMENT AND METHOD OF MANUFACTURING THE SAME

(75) Inventors: Seiji Yamada, Kanagawa (JP); Yoshio Goto, Kanagawa (JP); Yuichi Tokita, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/139,461

(22) PCT Filed: Dec. 10, 2009

(86) PCT No.: PCT/JP2009/070674
§ 371 (c)(1),
(2), (4) Date: Dec. 13, 2011

(87) PCT Pub. No.: WO2010/071071
PCT Pub. Date: Jun. 24, 2010

(65) Prior Publication Data
US 2012/0103798 A1    May 3, 2012

(30) Foreign Application Priority Data
Dec. 18, 2008 (JP) ............................... P2008-322199

(51) Int. Cl.
*G01N 33/544* (2006.01)
*G01N 33/551* (2006.01)

(52) U.S. Cl.
USPC .......................................... 436/535; 436/524

(58) Field of Classification Search
None
See application file for complete search history.

(56) References Cited

U.S. PATENT DOCUMENTS

| 7,482,624 B2 * | 1/2009 | Liljedahl et al. ............... 257/40 |
| 8,178,872 B2 * | 5/2012 | Tokita et al. .................. 257/40 |
| 2006/0046344 A1 | 3/2006 | Liljedahl et al. |
| 2012/0012823 A1 * | 1/2012 | Yamada et al. ................ 257/40 |

FOREIGN PATENT DOCUMENTS

| JP | HEI 10-280182 | 10/1998 |
| JP | 2005-345156 | 12/2005 |
| JP | 2006-296208 | 11/2006 |
| JP | 2007-220445 | 8/2007 |
| JP | 2008-122347 | 5/2008 |

OTHER PUBLICATIONS

Santos et al. Electrochemical studies on small electron transfer proteins using membrane electrodes. Journal of Electroanalytical Chemistry 2003, vol. 541, pp. 153-162.*

Japanese Patent Office, Notice of reasons for refusal (with English translation), issued in connection with Japanese Patent Application No. 2008-322199, dated Apr. 3, 2012. (4 pages).

(Continued)

*Primary Examiner* — Shafiqul Haq
(74) *Attorney, Agent, or Firm* — K&L Gates LLP

(57) ABSTRACT

In one example embodiment, a protein-immobilized electrode is stably used for long time. In one example embodiment, a method of manufacturing the protein-immobilized electrode includes immobilizing cytochrome c552 having high stability to a chemically-stable gold electrode while maintaining electron transfer capability of the cytochrome c552. In one example embodiment, a self-assembled monolayer is formed on a gold electrode by using hydrophobic thiol and hydrophilic thiol. By dipping the gold electrode on which the self-assembled monolayer is formed in a cytochrome c552 solution, a protein-immobilized electrode in which a cytochrome c552 is immobilized to the gold electrode with the self-assembled monolayer in between is produced.

3 Claims, 15 Drawing Sheets

(56) References Cited

OTHER PUBLICATIONS

Bernad, et al., "Characterization and Redox Properties of Cytochrome c552 from *Thermus thermophilus* Adsorbed on Different Self-Assembled Thiol Monolayers, Used to Model the Chemical Environment of the Redox partner," Biopolymers, vol. 81, pp. 407-418, 2006. (14 pages).

Japanese Patent Office, Non-patent literature cited, issued in connection with Japanese Patent Application No. 2008-322199, dated Apr. 3, 2012. (3 pages).

Bernad et al., "Kinetics of the electron transfer reaction of Cytochrome C552 absorbed on biomimetic electrode studied by time-resolved surface-enhanced resonance Raman spectroscopy and electrochemistry", Eur. Biophys. J., Oct. 2006, pp. 1039-1048, vol. 36.

Fee et al., "Integrity of *Thermus thermophilus* cytochrome C552 synthesized by *Escherichia coli* cells expressing the host-specific cytochrome c maturation genes, ecmABCDEFGH: Biochemical, spectral, and structural characterization of the recombinant protein", Protein Science, 2000, pp. 2074-2084.

Muresanu et al., "The Electron Transfer Complex between Cytochrome C552 and the CUA Domain of the *Thermus thermophilus* ba3 Oxidase", Journal of Biological Chemistry, May 19, 2006, pp. 14503-14513, vol. 281, No. 20.

Japanese Patent Office, Decision of Refusal issued in connection with Japanese Patent Application No. 2008-322199, dated Sep. 4, 2012. (8 pages).

Fujita et al., "Redox reactions of cyt. c and Azurin fixed on the mixed SAM modified Au electrodes" p. 77 (3 pages), Mar. 24, 2004.

State Intellectual Property Office of The People's Republic of China, Notification of the Second Office Action issued in connection with Chinese Patent Application Serial No. 200980154795.9, dated Oct. 21, 2013, (16 pages).

\* cited by examiner (A)            (B)

PROTEIN-IMMOBILIZED ELECTRODE AND METHOD OF MANUFACTURING THE SAME, AND FUNCTIONAL ELEMENT AND METHOD OF MANUFACTURING THE SAME

CROSS REFERENCE TO RELATED APPLICATIONS

The present application is a National Stage of International Application No. PCT/JP2009/070674 filed on Dec. 10, 2009, which claims priority to Japanese Patent Application No. 2008-322199 filed in the Japanese Patent Office on Dec. 18, 2008, the entire contents of which are being incorporated herein by reference.

BACKGROUND

In recent years, demand for a protein-immobilized electrode is increasing. For example, in an organism, an electron transfer reaction occurs among a number of protein couples. At the time of examining orientation and the mechanism of electron transfer in formation of a complex among the protein couples, a protein-immobilized electrode is used. In this case, the protein-immobilized electrode is used in such a manner that a protein is immobilized to an electrode and, only when a specific interaction occurs between the protein and another protein, current is detected through the protein-immobilized electrode.

Moreover, in recent years, attention is being paid to use of protein for a photoelectric conversion element. For example, it is taught that photocurrent is obtained from a protein-immobilized electrode in which zinc cytochrome c (which is obtained by substituting iron of horse-heart cytochrome c with zinc) is immobilized to a gold electrode, and a photoelectric conversion element using the protein-immobilized electrode is proposed (refer to patent document 1). However, protein is unstable on the outside of a living organism. Therefore, if long-term stabilization of the photoelectric conversion element is achieved, it is very significant. However, as far as the inventors of the present disclosure know, there is no such a report until now.

Thermusthermophilus-derived cytochrome c552 functions as an electron transfer member in a living organism in a manner similar to the horse-heart cytochrome c. It is known that cytochrome c552 has thermal stability which is much higher than that of horse-heart cytochrome c (refer to non-patent document 1). For example, the denaturation midpoint of general protein is 50 to 60° C. and that of horse-heart cytochrome c is 85° C. On the other hand, the denaturation temperature of cytochrome c552 is immeasurable in a general solution (the upper limit of temperature is 100° C.) and is 100° C. or higher. Moreover, it is reported that the denaturation midpoint of cytochrome c552 in the presence of 4.2M of guanidinium hydrochloride (denaturation agent) is 60 to 70° C.

Because cytochrome c552 has high thermal stability as described above, it is suitable as a device material. Although cytochrome c552 and horse-heart cytochrome c have similar constituent amino acids and similar three-dimensional structures but their environments of an active center heme pocket in which electron transfer is performed are different. Concretely, in the horse-heart cytochrome c, lysine residues having positive charges are dispersed in the entire molecule. In the cytochrome c552, although the number of lysine residues is similar to that in the horse-heart cytochrome c, the lysine residues are not disposed around the heme pocket. It is reported that a complex of cytochrome c552 and its in-vivo redox partner is formed mainly by hydrophobic interaction, according to the structure of the complex (refer to non-patent document 2). Therefore, to immobilize cytochrome c552 to an electrode while maintaining its electron transfer capability, its specific condition search is necessary.

One of known methods for immobilizing horse-heart cytochrome c to an electrode uses a monomolecular film (HS (CH$_2$)$_{10}$COO—, 1-carboxy-10-decanethiol). Consequently, it is considered to use the immobilization method for the immobilization of cytochrome c552. However, in the method of immobilizing cytochrome c552 to an electrode by using a monomolecular film used in the method for immobilizing horse-heart cytochrome c, an oxidation-reduction current of cytochrome c552 has not been obtained so far.

A French study group reported that they successfully obtained a protein-derived oxidation-reduction current by using a protein-immobilized electrode in which cytochrome c552 is immobilized on a silver electrode (refer to non-patent document 3). However, in a cyclic voltammogram obtained using the protein-immobilized electrode, a peak separation between an oxidation wave and a reduction wave is significant, so that there is a problem in protein orientation control. In addition, silver as the electrode material is susceptible to corrosion and oxidation even in use in a normal environment. That is, because the silver electrode is unsuitable for long-term stable use, it is preferable to use a chemically stable electrode instead of a silver electrode.

CITATION LIST

Patent Document

Patent document 1: Japanese Unexamined Patent Application Publication No. 2007-220445

Non-Patent Documents

Non-patent document 1: Fee, J. A. and 13 others, Protein Sci. 9, 2074 (2000)
Non-patent document 2: Muresanu, L. and 13 others, J. Biol. Chem. 281, 14503 (2006)
Non-patent document 3: Bernad, S. and 3 others, Eur. Biophys. J. 36, 1039 (2007)

SUMMARY

Therefore, a problem to be solved by the present disclosure is to provide a protein-immobilized electrode which is stably used for long time and a method of manufacturing the same in which cytochrome c552 or its derivative or variant having high stability is immobilized to a chemically-stable gold electrode while maintaining electron transfer capability of the cytochrome c552 or its derivative or variant.

Another problem to be solved by the present disclosure is to provide a functional element using a protein-immobilized electrode which is stably used for long time and a method of manufacturing the same in which cytochrome c552 or its derivative or variant having high stability is immobilized to a chemically-stable gold electrode while maintaining electron transfer capability of the cytochrome c552 or its derivative or variant.

The inventors of the present disclosure keenly studied to solve the problems, found out by chance that cytochrome c552 can be immobilized to a gold electrode without deteriorating the electron transfer capability of cytochrome c552, and devised the present disclosure.

Specifically, to solve the problems, the present disclosure is a protein-immobilized electrode comprising a gold electrode, and cytochrome c552 or its derivative or variant immobilized to the gold electrode.

The present disclosure is also a method of manufacturing a protein-immobilized electrode comprising immobilizing cytochrome c552 or its derivative or variant to a gold electrode.

The present disclosure is also a functional element having a protein-immobilized electrode including a gold electrode, and cytochrome c552 or its derivative or variant immobilized to the gold electrode.

The present disclosure is also a method of manufacturing a functional element, including the step of forming a protein-immobilized electrode by immobilizing cytochrome c552 or its derivative or variant to a gold electrode.

Herein, the functional element is not limited as long as it uses cytochrome c552 or its derivative or variant. Examples of the functional element include photoelectric conversion elements and various electron elements having the photoelectric conversion function.

In the present disclosure, cytochrome c552 or its derivative or variant is typically immobilized in such a manner that the hydrophobic part is opposed to the gold electrode side. Typically, the cytochrome c552 or its derivative or variant and the gold electrode are coupled to each other with a self-assembled monolayer in between. A derivative of cytochrome c552 is cytochrome c552 having a chemically modified amino acid residue or heme in the skeleton of cytochrome c552. A variant of cytochrome c552 is obtained by substituting a part of an amino acid residue in the skeleton of cytochrome c552 with another amino acid residue.

In the present disclosure constructed as described above, because the gold electrode is chemically stable, occurrence of corrosion, oxidation, or the like of a protein-immobilized electrode when used is prevented. In addition, the electron transfer capability of cytochrome c552 or its derivative or variant is not deteriorated at the time of immobilizing cytochrome c552 or its derivative or variant to a gold electrode.

According to the present disclosure, a protein-immobilized electrode which is stably used for long time and in which cytochrome c552 or its derivative or variant having high stability is immobilized to a chemically-stable gold electrode while maintaining electron transfer capability of the cytochrome c552 or its derivative or variant can be realized. In addition, various high-performance functional elements are realized by using the protein-immobilized electrode.

Additional features and advantages are described herein, and will be apparent from the following Detailed Description and the figures.

DETAILED DESCRIPTION

Best modes for carrying out the disclosure (hereinbelow, called embodiments) will be described below.

Note that the description will be given in the following order.

1. First Example Embodiment (a protein immobilized electrode and a method of manufacturing the same)

2. Second Example Embodiment (photoelectric conversion element)

1. First Example Embodiment

Protein Immobilized Electrode

Figure 1:
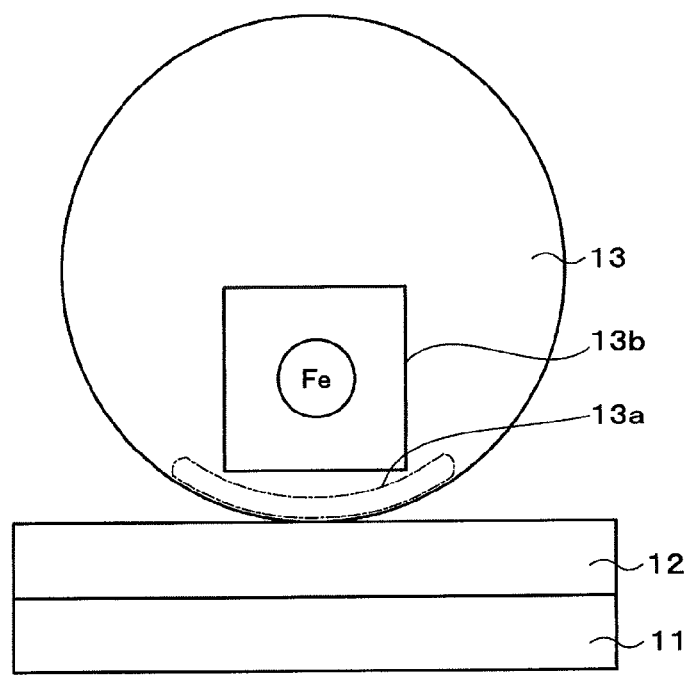
FIG. 1 is a schematic diagram illustrating a protein immobilized electrode according to a first example embodiment of the present disclosure.

FIG. 1 illustrates a protein immobilized electrode according to a first example embodiment.

As illustrated in FIG. 1, in the protein immobilized electrode, cytochrome c552 13 is immobilized on a gold electrode 11 with a self-assembled monolayer (SAM) 12 in between. In this case, the cytochrome c552 13 is immobilized so that its hydrophobic part 13a is the gold electrode 11 side. To a heme 13b in the cytochrome c552 13, iron (Fe) is coordinated as a central metal.

Figure 2:
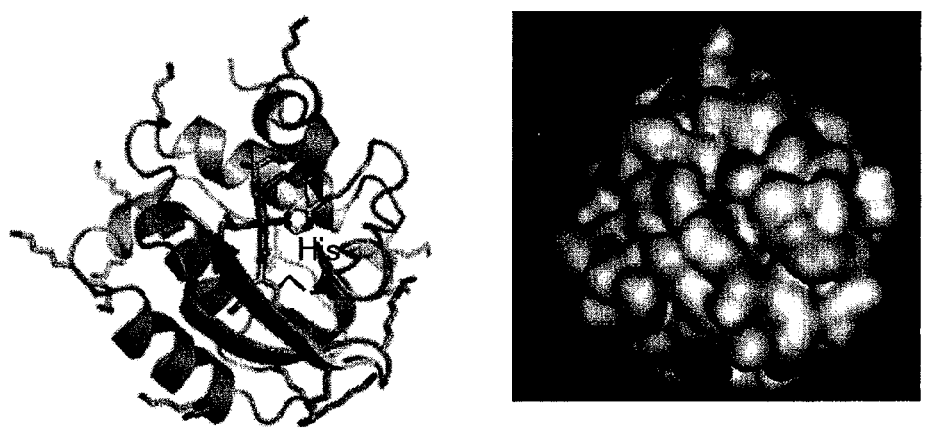
FIG. 2 is schematic diagrams illustrating the structure of cytochrome c552 used in the protein immobilized electrode according to the first example embodiment of the disclosure.
Figure 3:
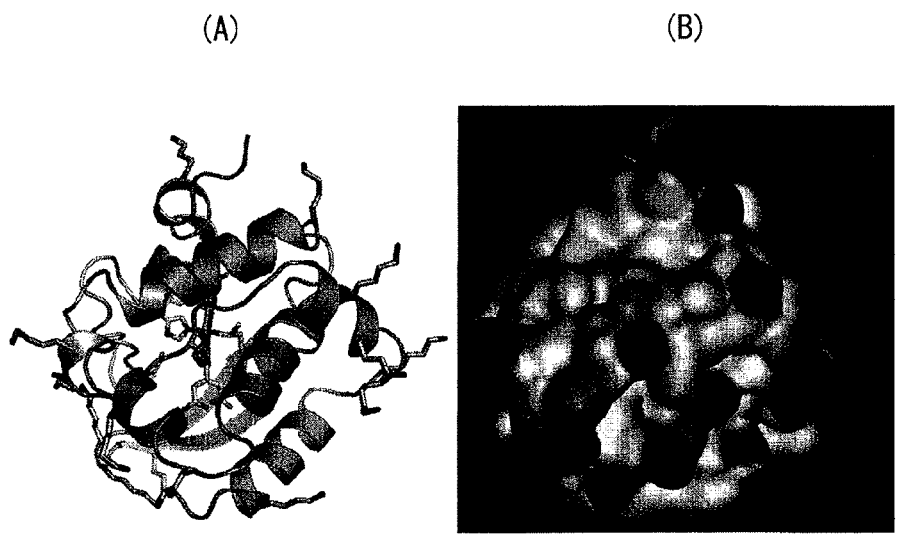
FIG. 3 is schematic diagrams illustrating the structure of cytochrome c552 used in the protein immobilized electrode according to the first example embodiment of the disclosure.

FIG. 2A schematically illustrates the structure of the cytochrome c552. FIG. 2A illustrates a stick model of a hem of cytochrome c552 and its axial ligand histidine (His), methionine (Met), and lysine residues (positively charged amino acid). FIG. 2A is a front view of the heme of cytochrome c552, which is oriented such that the axial ligand histidine (His) is positioned on the right side. FIG. 2B is a surface charge distribution diagram of the cytochrome c552 illustrated in FIG. 2A. FIG. 3A is a diagram of the cytochrome c552 viewed from the back side of the heme. FIG. 3B is a surface charge distribution diagram of the cytochrome c552 illustrated in FIG. 3A.

Figure 4:
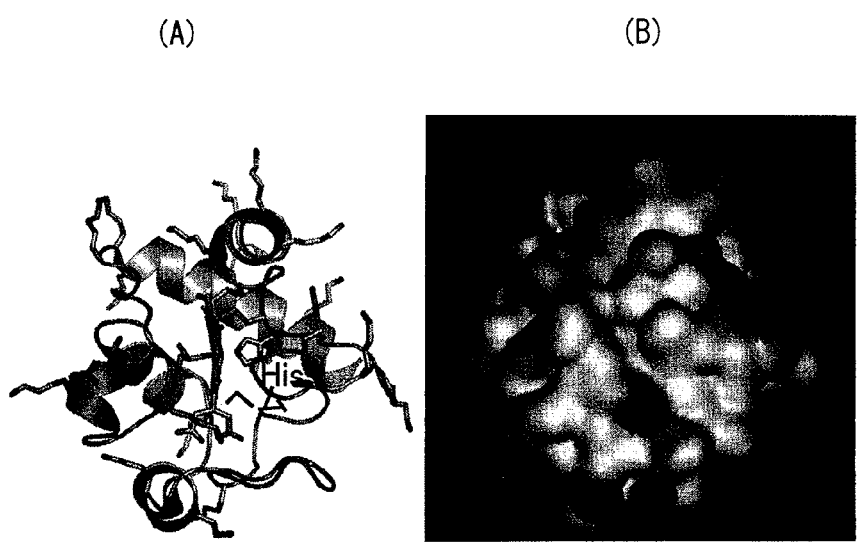
FIG. 4 is schematic diagrams illustrating the structure of horse-heart cytochrome c.
Figure 5:
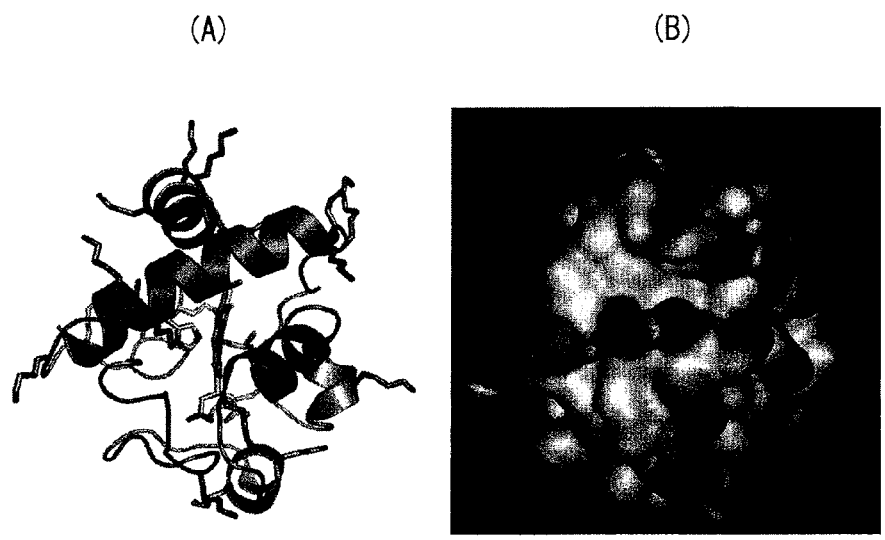
FIG. 5 is schematic diagrams illustrating the structure of horse-heart cytochrome c.

For comparison, FIG. 4A is a diagram of horse-heart cytochrome c viewed from the front side of the heme, and FIG. 4B is a surface charge distribution diagram of the horse-heart cytochrome c in FIG. 4A. FIG. 5A is a diagram of the horse-heart cytochrome c viewed from the back side of the heme, and FIG. 5B is a surface charge distribution diagram of horse-heart cytochrome c illustrated in FIG. 5A.

As illustrated in FIGS. 4B and 5B, the horse-heart cytochrome c has positive charges dispersed over the entire molecule. On the other hand, as illustrated in FIGS. 2B and 3B, cytochrome c552 has positive charges concentrated in the back of the heme. In addition, the front of the heme of the cytochrome c552 is occupied by hydrophobic residues and neutral polar residues. The hydrophobic part 13a of the cytochrome c552 13 corresponds to that front portion of the heme.

Figure 6:
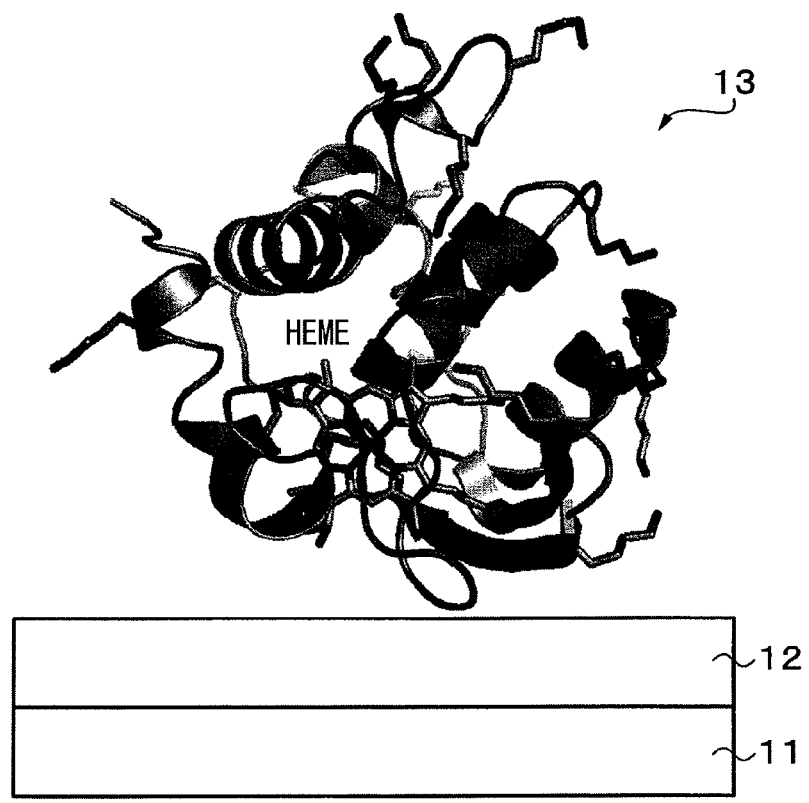
FIG. 6 is a schematic diagram illustrating the details of the structure of cytochrome c552 of the protein immobilized electrode according to the first example embodiment of the disclosure.

FIG. 6 schematically illustrates the cytochrome c552 13 immobilized to the gold electrode 11 with the self-assembled molecular monolayer 12 in between. In FIG. 6, the axial ligand histidine exists in front of the cytochrome c552 13, and the lysine residues are illustrated by a stick model.

Figure 7:
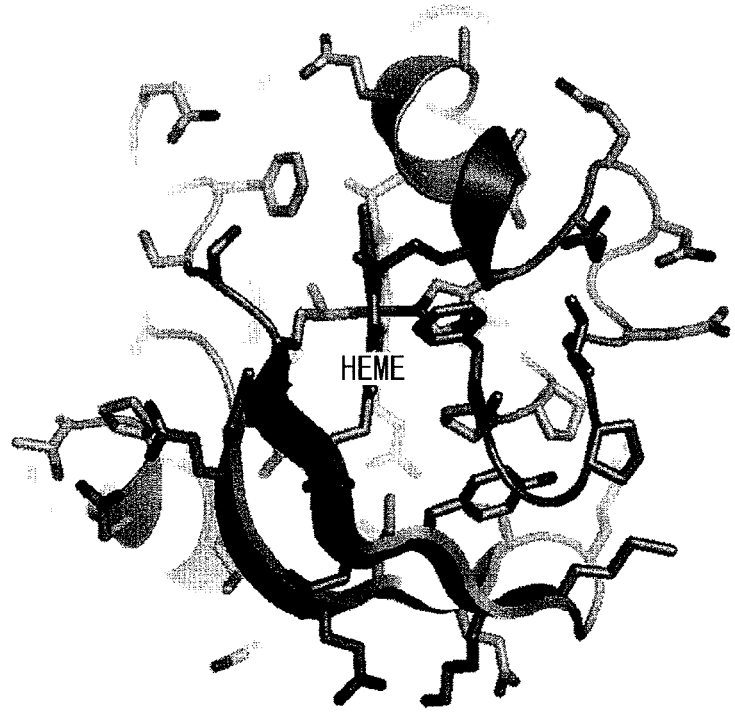
FIG. 7 is a schematic diagram illustrating the details of the structure of cytochrome c552 of the protein immobilized electrode according to the first example embodiment of the disclosure.

FIG. 7 is a diagram of the cytochrome c552 13 immobilized to the gold electrode 11 with the self-assembled monolayer 12 in between, which is viewed from the gold electrode 11 side, where the axial ligand histidine exists on the right side (the front of the heme). In FIG. 7, amino-acid-side chains are indicated by a stick model.

The self-assembled monolayer 12 is made of three parts. A first part is a bonding functional group (such as a thiol group (—SH)) that reacts with an atom in the surface of the gold electrode 11 to which the self-assembled monolayer 12 is to be immobilized. A second part is typically an alkyl chain. The two-dimensional regular structure of the self-assembled monolayer 12 is determined mainly by the Van der Waals forces between the alkyl chains. Accordingly, in general, in the case where the carbon number of the alkyl chains is reasonably large, a stable, highly-dense, and highly-oriented film is formed. A third part is a terminal group. By using the terminal group as the functional group, the solid surface is functionalized.

The self-assembled monolayer 12 is formed using, for example, a hydrophobic thiol and a hydrophilic thiol. According to the proportion of the hydrophobic thiol and the hydrophilic thiol, the easiness of bonding between the cytochrome c552 13 and the gold electrode 11 varies. Examples of the hydrophilic group of the hydrophilic thiol include —OH, —$NH_2$, $SO_3^-$, $OSO_3^-$, $COO^-$, and $NH_4^+$. The hydrophobic thiol and the hydrophilic thiol may be selected as necessary.

A preferred example of the combination of the hydrophobic thiol and the hydrophilic thiol is a combination of $HS(CH_2)_nCH_3$ (n=5, 8, 10) as the hydrophobic thiol and $HS(CH_2)_nCH_2OH$ (n=5, 8, 10) as the hydrophilic thiol. Concretely, for example, the hydrophobic thiol is 1-undecanethiol ($HS(CH_2)_{10}CH_3$), and the hydrophilic thiol is 1-hydroxy-11-undecanethiol ($HS(CH_2)_{10}CH_2OH$). Another example of the combination of the hydrophobic thiol and the hydrophilic thiol is a combination of $HS(CH_2)_mCH_3$ as the hydrophobic thiol and $HS(CH_2)_nCH_2OH$ as the hydrophilic thiol (where m<n, m is, for example, five or larger, and n is, for example, 10 or less). Concretely, for example, the hydrophobic thiol is $HS(CH_2)_9CH_3$, and the hydrophilic thiol is $HS(CH_2)_{10}CH_2OH$.

Figure 8:
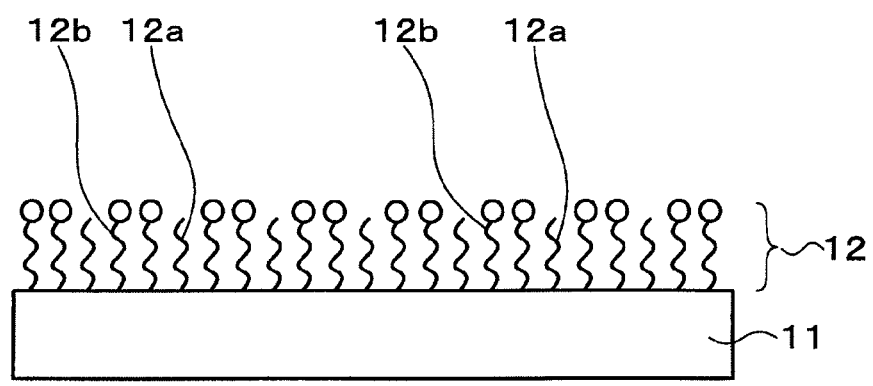
FIG. 8 is a schematic diagram illustrating the structure of a self-assembled monolayer in the protein immobilized electrode according to the first example embodiment of the disclosure.

FIG. 8 schematically shows the structure of the self-assembled monolayer 12 formed using the hydrophobic thiol and the hydrophilic thiol. As shown in FIG. 8, the thiol group (—SH) side of a hydrophobic thiol 12a and a hydrophilic thiol 12b is bonded to the surface of the gold electrode 11. In addition, the hydrophobic group side of the hydrophobic thiol 12a and the hydrophilic group side of the hydrophobic thiol 12b (indicated by circles in FIG. 8) is bonded to the hydrophobic part 13a of the cytochrome c552 13.

Method for Producing Protein-Immobilized Electrode

An example of a method for producing the protein-immobilized electrode will be described.

First, the gold electrode 11 is dipped in a solution obtained by mixing the hydrophobic thiol and the hydrophilic thiol at a predetermined ratio (using, for example, ethanol as a solvent) to form the self-assembled monolayer 12 on the surface of the gold electrode 11, as shown in FIG. 1.

Next, the gold electrode 11 on which the self-assembled monolayer 12 is formed is dipped in a solution containing the cytochrome c552 13, a buffer solution and, as necessary, a salt such as potassium chloride (KCl). As a result, the cytochrome c552 13 is adsorbed and immobilized on the self-assembled monolayer 12 so that the hydrophobic part 13a faces the gold electrode 11 side.

In such a manner, the protein-immobilized electrode as a target is manufactured.

Example

An example of the protein-immobilized electrode (hereinbelow, called cytochrome c552 immobilized electrode) will be described.

1. Production of Sample

Prepared was a 0.1 mM ethanol solution obtained by mixing 1-undecanethiol ($HS(CH_2)_{10}CH_3$) as a hydrophobic thiol and 1-hydroxy-11-undecanethiol ($HS(CH_2)_{10}CH_2OH$) as a hydrophilic thiol at a ratio of 25:75. A clean gold drop electrode or gold planar electrode was then dipped in the solution and left at room temperature for one day. In such a manner, a self-assembled monolayer was formed on the surface of the gold drop electrode or the gold planar electrode.

The electrode was rinsed with ultrapure water, dipped in a 50 μM cytochrome c552 solution (10 mM tris-hydrochloric acid buffer solution (pH 7.6) and 50 mM KCl), and incubated at room temperature for 30 minutes or longer. In such a manner, a cytochrome c552 immobilized electrode in which cytochrome c552 is immobilized to the surface of the gold drop electrode or the gold planar electrode with the self-assembled monolayer in between was produced.

Figure 9:
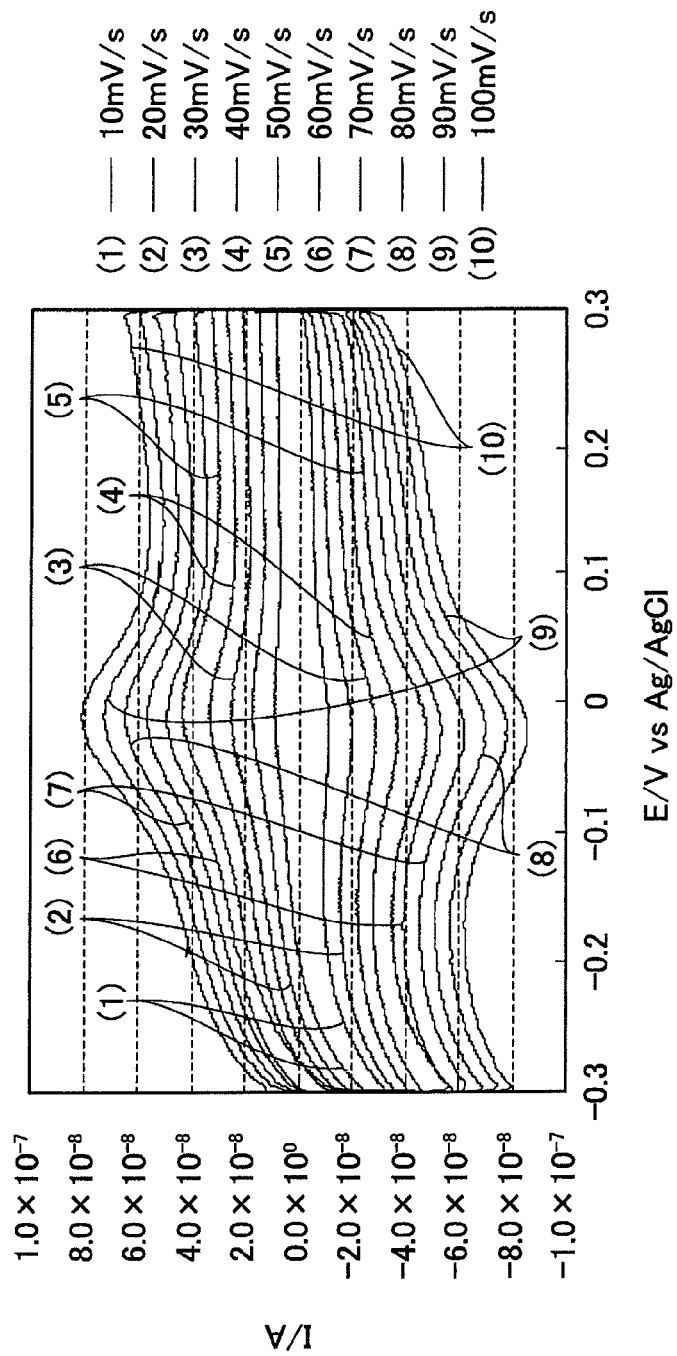
FIG. 9 is a schematic diagram illustrating results of cyclic voltammetry performed using a cytochrome c552 immobilized electrode in an example.
Figure 10:
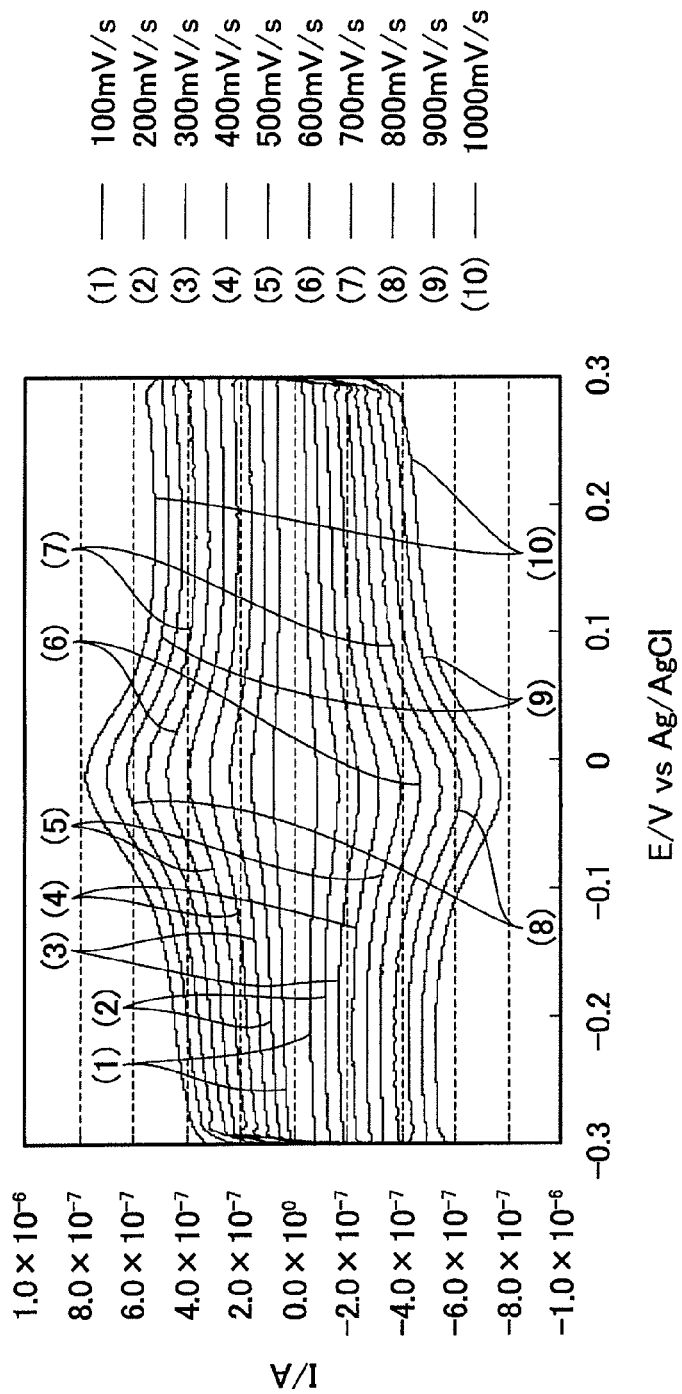
FIG. 10 is a schematic diagram illustrating results of cyclic voltammetry performed using a cytochrome c552 immobilized electrode in an example.

Using the cytochrome c552 immobilized electrode produced as described above, cyclic voltammetry was carried out. The results are shown in FIGS. 9 and 10. In FIGS. 9 and 10, I denotes current (A), and E indicates the potential (V) for a reference electrode (Ag/AgCl) (the same applies hereinafter). It is understood from FIGS. 9 and 10 that typical adsorptive cyclic voltammograms without peak separation are drawn. Here, the cyclic voltammogram illustrated in FIG. 9 shows the results of measurement carried out at potential sweep rates varied by 10 mV/s in the range of 10 to 100 mV/s. Moreover, the cyclic voltammogram illustrated in FIG. 10 indicates the results of measurement carried out at potential sweep rates varied by 100 mV/s in the range of 100 to 1,000 mV/s.

As understood from FIGS. 9 and 10, in the cytochrome c552 immobilized electrode, no peak separation occurs in the range of the potential sweep rate of 10 to 1,000 mV/s. It denotes that the heme pocket of cytochrome c552 is optimally coordinated to the gold electrode in the cytochrome c552 immobilized electrode.

Figure 11:
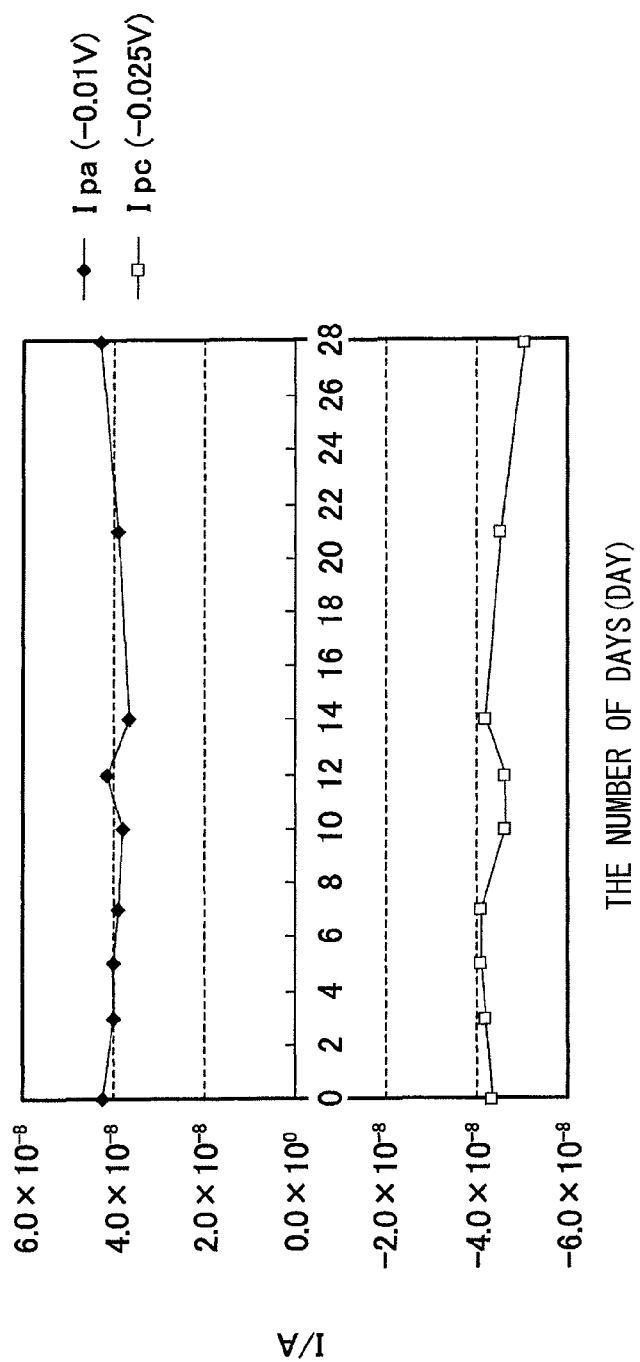
FIG. 11 is a schematic diagram showing variation per day in current values when the cytochrome c552 immobilized electrode in the example was stored in a protein solution at room temperature.

FIG. 11 illustrates variation per day in current values (anodic current Ipa and cathodic current Ica) occurring when the cytochrome c552 immobilized electrode was stored in a protein solution at room temperature. As illustrated in FIG. 11, the cytochrome c552 immobilized electrode obtains the same oxidation-reduction current value even after being stored in the protein solution at room temperature for one month. In contrast, in a similar experiment using horse-heart cytochrome c, the current value decreased gradually with lapse of time, and peak separation occurred in the cyclic voltammogram.

Next, comparison data in the case where the direction of the heme of cytochrome c552 in the cytochrome c552 immobilized electrode is opposite to that of the heme of cytochrome c552 in the cytochrome c552 immobilized electrode in the example, that is, that of the gold electrode will be described. More concretely, data in the case where cytochrome c552 is immobilized on the gold electrode using a self-assembled monolayer having a different terminal, that is, the case where cytochrome c552 is immobilized in a wrong orientation, will be described.

Figure 12:
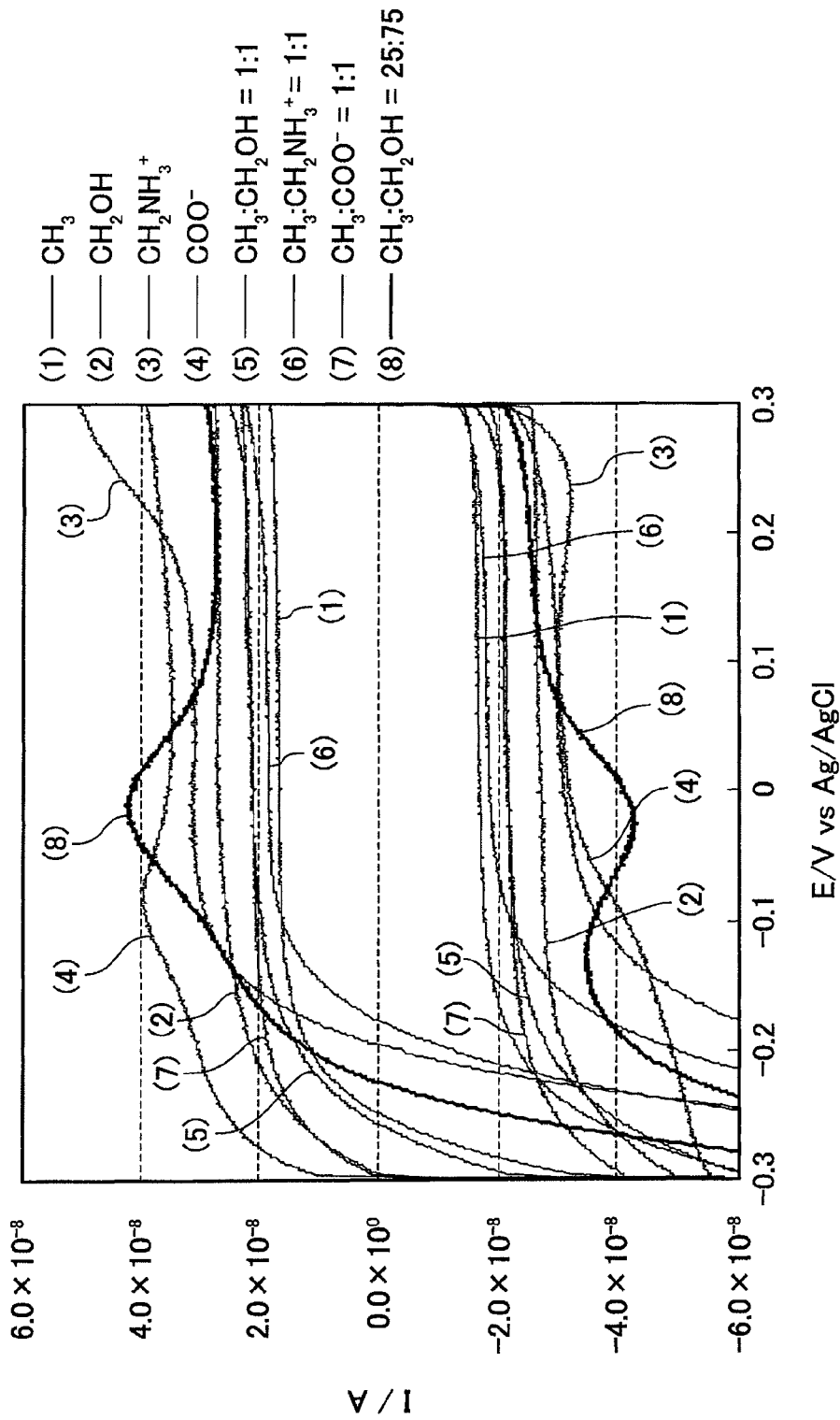
FIG. 12 is a schematic diagram illustrating results of cyclic voltammetry performed using the cytochrome c552 immobilized electrode in the example.

Concretely, cyclic voltammetry was carried out using cytochrome c552 immobilized electrodes having cytochrome c552 immobilized on gold electrodes using thiols ($HS(CH_2)_{10}R$) having ten carbon atoms and different terminals (—R). The resultant cyclic voltammograms are shown in FIG. 12, where a 10 mM sodium phosphate solution (pH 7.0) was used as a buffer solution and the potential sweep rate was 50 mV/s. In FIG. 12, although peaks of oxidation reduction of protein or the like are seen in the case where the terminal (—R) was —COO—, after repetition of the oxidation-reduction cycle, the peaks disappear. It is consequently understood that in the case where cytochrome c552 is immobilized to the gold electrode in a wrong orientation, the function of cytochrome c552 is not maintained.

Next, the results of cyclic voltammetry carried out while varying KCl concentration in a cytochrome c552 solution used at the time of producing the above-described cytochrome c552 immobilized electrode will be described.

At the time of measurement, a 10 mM sodium phosphate solution (pH 7.0) was used as a buffer solution, and the potential sweep rate was set to 50 mV/s. The cytochrome c552 immobilized electrodes in each of which cytochrome c552 was immobilized to a gold drop electrode with a self-assembled monolayer in between formed using $HS(CH_2)_{10}CH_3$ and $HS(CH_3)_{10}CH_2OH$ in a manner similar to the above were used. In this regard, the diameter of the gold drop electrode was 2.5 mm.

Figure 13:
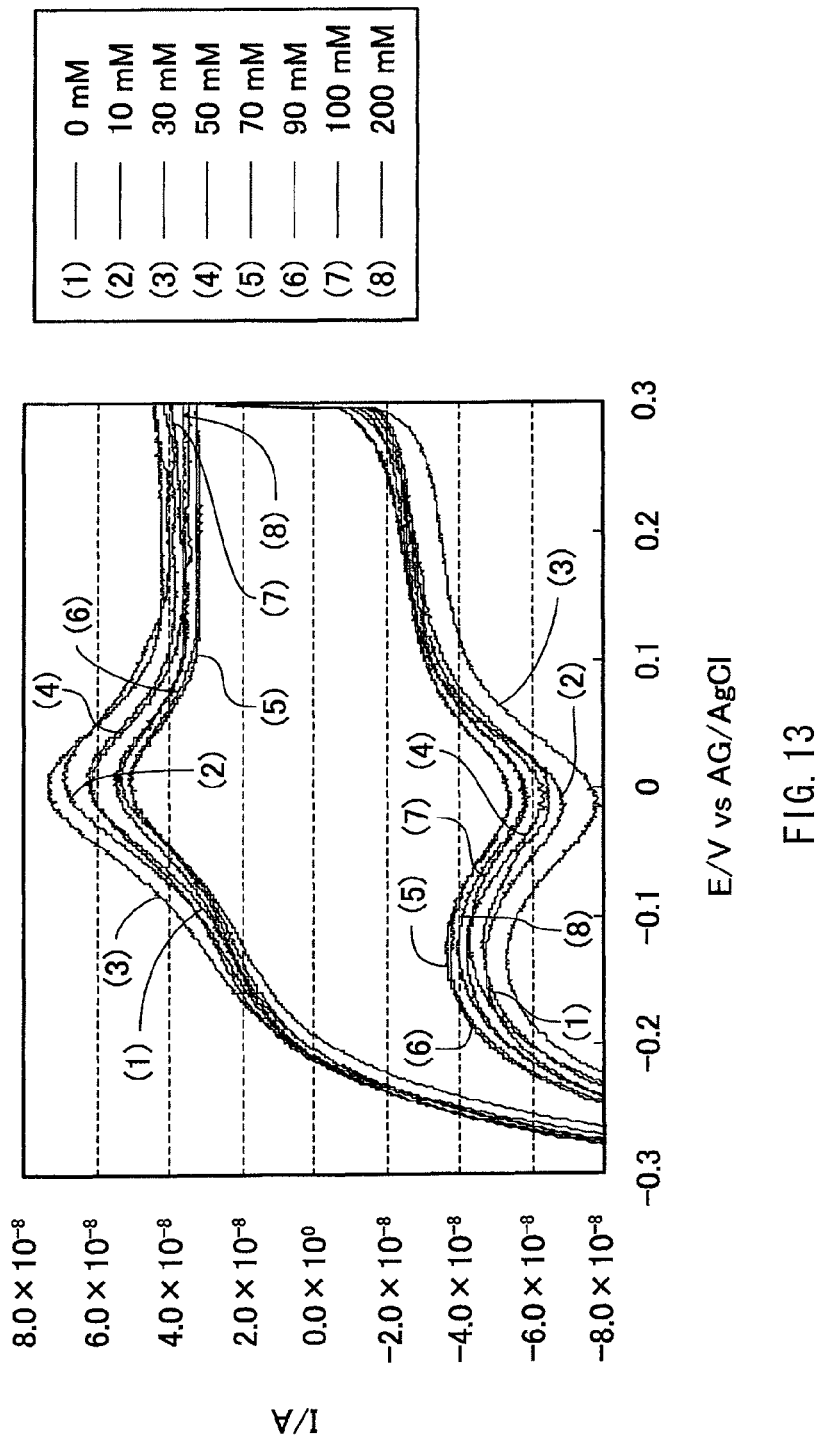
FIG. 13 is a schematic diagram illustrating results of cyclic voltammetry performed using the cytochrome c552 immobilized electrode in the example.

The resultant cyclic voltammograms are shown in FIG. 13. In this regard, a 10 mM tris-hydrochloric acid buffer solution (pH 7.6) was used as the buffer solution in the cytochrome c552 solution. Because the range of KCl concentration in the cytochrome c552 solutions capable of immobilizing cytochrome c552 is 0 to 200 mM, the cyclic voltammetry was carried out while varying the KCl concentration in the range.

Figure 14:
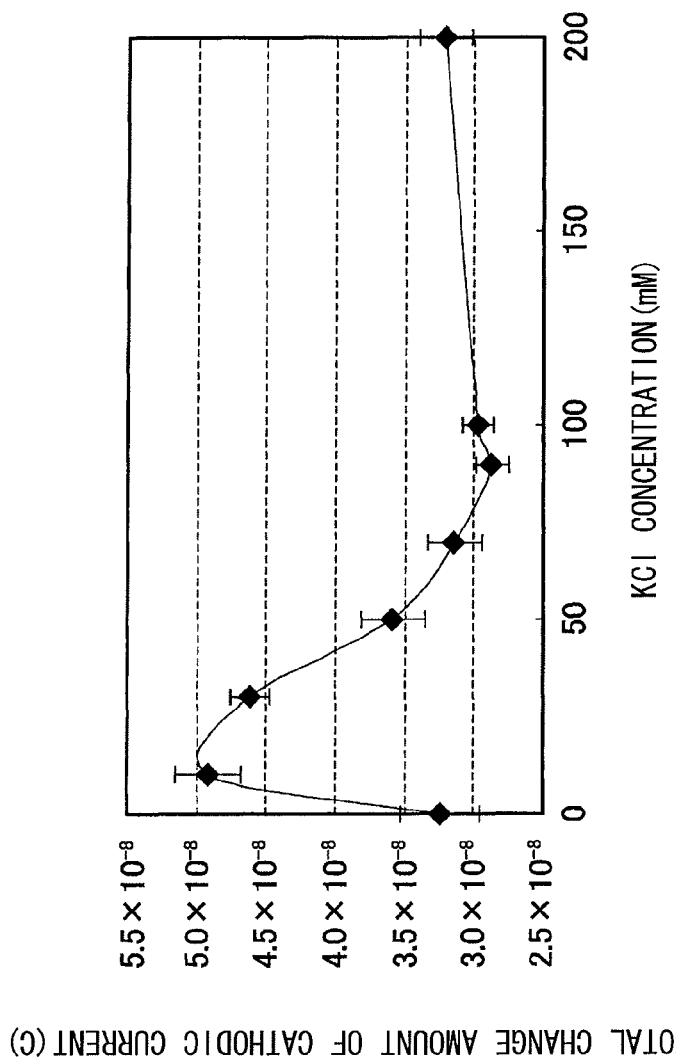
FIG. 14 is a schematic diagram illustrating results of the cyclic voltammetry performed using cytochrome c552 immobilized electrodes produced while changing the KCl concentration in a cytochrome c552 solution.

FIG. 14 is a graph obtained by integrating the cathodic current (downward peak) of the cyclic voltammograms shown in FIG. 13 to obtain a total charge amount and then plotting the amount with respect to the KCl concentration. It is understood from FIG. 14 that the optimum KCl concentration is the range of 10 to 30 mM. When the concentration falls within the optimum range, the immobilization amount of cytochrome c552 is about 1.5 times as large as that in the case where the cytochrome c552 solution contains no KCl, that is, the KCl concentration is 0 mM, or that in the case where the KCl concentration is 50 mM or higher. In the case where the KCl concentration is higher than 100 mM, desorption of cytochrome c552 and the self-assembled monolayer appears.

Subsequently, self-assembled monolayers were formed while varying the ratio between $HS(CH_2)_{10}CH_3$ and $HS(CH_2)_{10}CH_2OH$ in an ethanol solution obtained by mixing $HS(CH_2)_{10}CH_3$ and $HS(CH_2)_{10}CH_2OH$, used at the time of forming the self-assembled monolayer. Then, the cyclic voltammetry was performed on cytochrome c552 immobilized electrodes formed by immobilizing cytochrome c552 to the gold electrode with the self-assembled monolayer in between. In this regard, at the time of measurement, a 10 mM sodium phosphate solution (pH 7.0) was used as a buffer solution, and the potential sweep rate was set to 50 mV/s.

Figure 15:
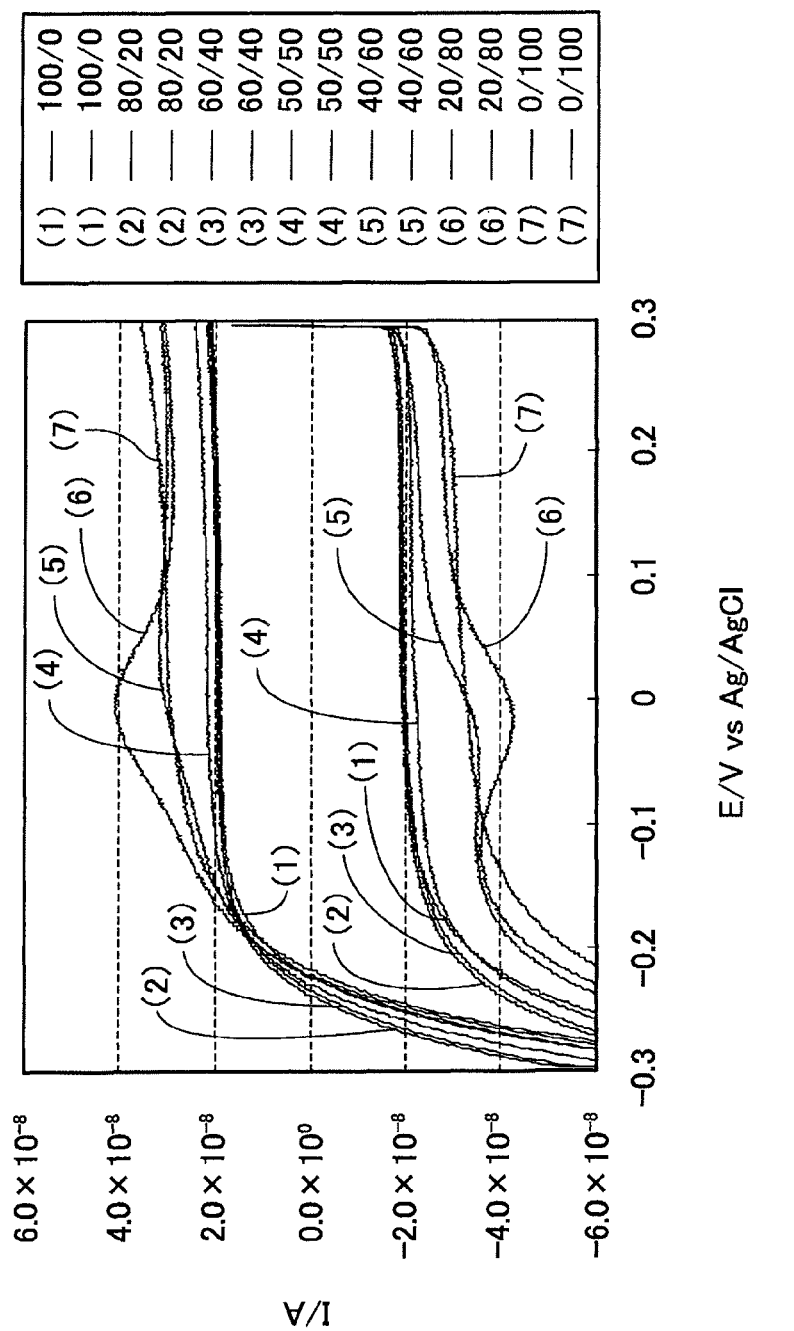
FIG. 15 is a schematic diagram illustrating results of the cyclic voltammetry performed using cytochrome c552 immobilized electrodes produced while changing the content of $HS(CH_3)_{10}CH_2OH$ used for formation of a self-assembled monolayer.

The resultant cyclic voltammograms are shown in FIG. 15. The numerals in the footnote represent ($[HS(CH_2)_{10}CH_3]/[HS(CH_2)_{10}CH_2OH]$). For example, (20/80) denotes that $HS(CH_2)_{10}CH_3$ is 20% and $HS(CH_2)_{10}CH_2OH$ is 80%.

Based on the results illustrated in FIG. 15, examination was carried out by finely changing the content of $HS(CH_2)_{10}CH_2OH$ in the total amount of $HS(CH_2)_{10}CH_3$ and $HS(CH_2)_{10}CH_2OH$ in steps of 5% in the range of 60% to 95% both inclusive. The results are illustrated in FIG. 16.

Figure 16:
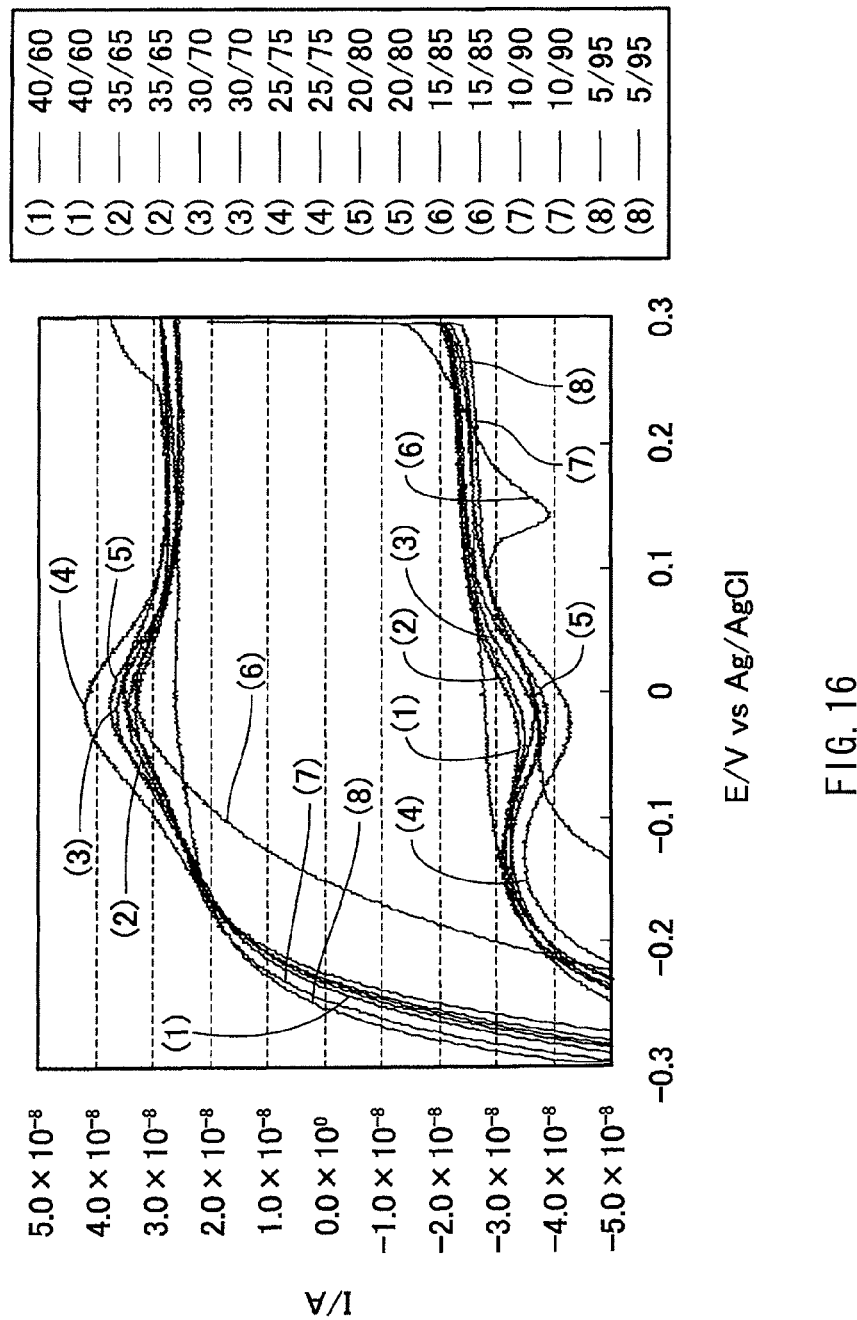
FIG. 16 is a schematic diagram illustrating results of the cyclic voltammetry performed using cytochrome c552 immobilized electrodes produced while changing the content of $HS(CH_3)_{10}CH_2OH$ used for formation of a self-assembled monolayer.
Figure 17:
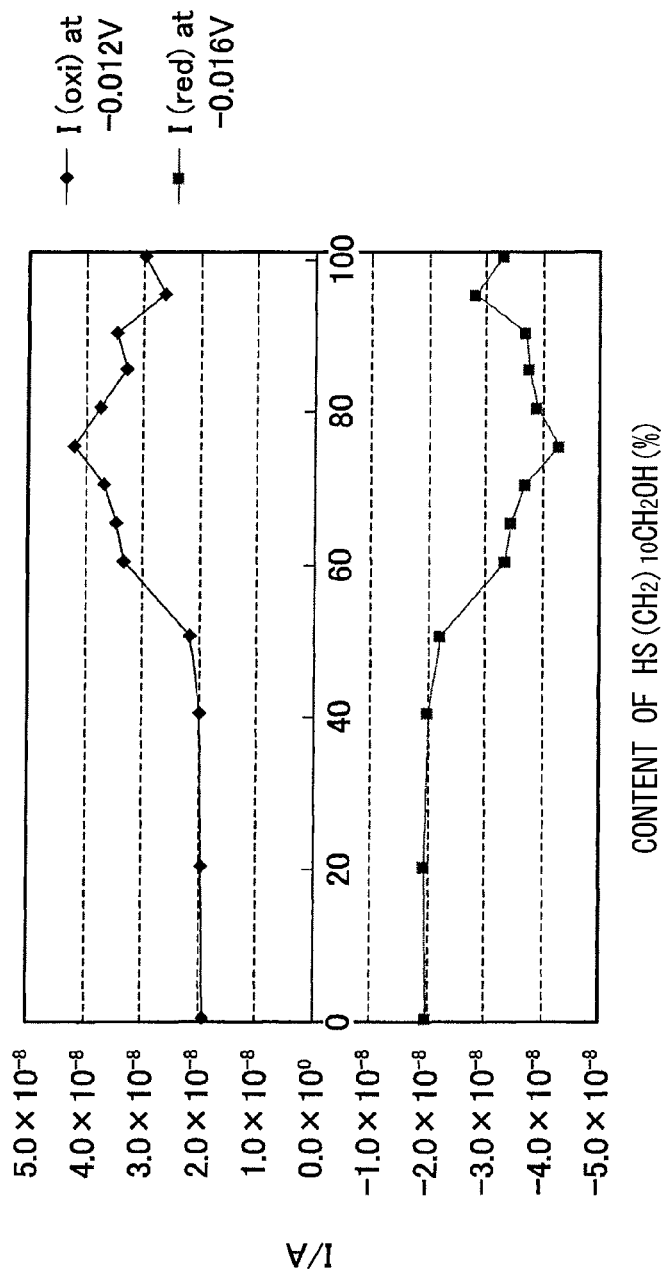
FIG. 17 is a schematic diagram obtained by plotting current values at peaks in cyclic voltammograms obtained by cyclic voltammetry performed by using cytochrome c552 immobilized electrodes produced while changing the content of $HS(CH_3)_{10}CH_2OH$ in a material used for formation of a self-assembled monolayer, with respect to the content of $HS(CH_3)_{10}CH_2OH$.

FIG. 17 is a graph obtained by plotting current values at oxidation-reduction peaks in the results illustrated in FIGS. 15 and 16 with respect to the content of $HS(CH_2)_{10}CH_2OH$. It is understood from FIG. 17 that cytochrome c552 is excellently immobilized when the content of $HS(CH_2)_{10}CH_2OH$ falls within the range of 60% to 90% both inclusive. Although the details are not described, from another experiment conducted, it was confirmed that cytochrome c552 is excellently immobilized when the content of $HS(CH_2)_{10}CH_2OH$ falls within the range of 60% to 90% both inclusive in all of the cases where the hydrophobic thiol is $HS(CH_2)_nCH_3$ (n=5, 8, 10) and the hydrophilic thiol is $HS(CH_2)_nCH_2OH$ (n=5, 8, 10).

Figure 18:
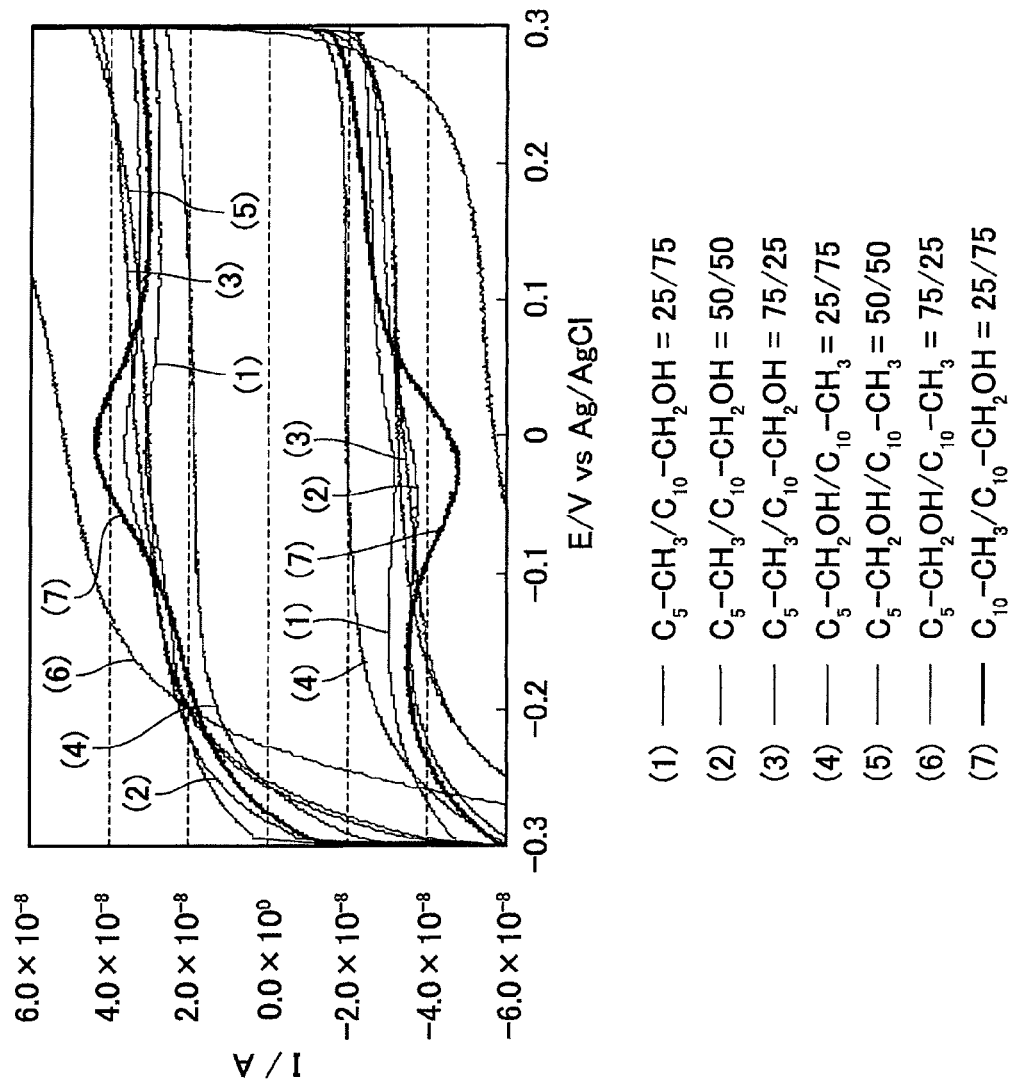
FIG. 18 is a schematic diagram illustrating results of the cyclic voltammetry performed using cytochrome c552 immobilized electrodes produced while changing the length of hydrophobic thiol and hydrophilic thiol used for formation of a self-assembled monolayer.

Next, the results of cyclic voltammetry carried out while varying lengths of hydrophobic thiols and hydrophilic thiols used at the time of forming self-assembled monolayers will be described. Concretely, the self-assembled monolayers were formed using combinations of $HS(CH_2)_5CH_3$ or $HS(CH_2)_{10}CH_3$ having a methyl-group terminal and whose carbon number is five or 10 as a hydrophobic thiol and $HS(CH_2)_{10}CH_2OH$ or $HS(CH_2)_5CH_2OH$ having a hydroxymethyl-group terminal and whose carbon number is five or 10. Cytochrome c552 was then immobilized to the gold electrode with the self-assembled monolayer in between. The cyclic voltammetry was conducted using the cytochrome c552 immobilized electrodes formed as described above. FIG. 18 illustrates obtained cyclic voltammograms.

In curves (1), (2), (3), and (7) illustrated in FIG. 18, peaks derived from protein appear around 0V. It shows that cytochrome c552 is immobilized in a similar orientation even when the carbon number of the hydrophobic thiol and the hydrophilic thiol is changed if the balance is maintained between the methyl group of the hydrophobic thiol and the hydroxyl group of the hydrophilic thiol in the hydrophobic thiol and the hydrophilic thiol used at the time of forming the self-assembled monolayer, that is, the balance between the distributions of the hydrophobic group and the hydrophilic group on the surface of the self-assembled monolayer. As for the hydrophilic thiol, an excellent result was obtained in the case where the carbon number of the hydrophilic group is 10 more than the case where the carbon number is five.

As described above, according to the first example embodiment, the cytochrome c552 13 having high stability is immobilized to the gold electrode 11 which is chemically stable with the self-assembled monolayer 12 in between so that the hydrophobic part 13a faces the gold electrode 11 side. Thus, the protein-immobilized electrode which is stably used for long time, in which the cytochrome c552 13 is immobilized on the gold electrode 11 while maintaining its electron transfer capability is realized.

2. Second Example Embodiment

Photoelectric Conversion Element

Figure 19:
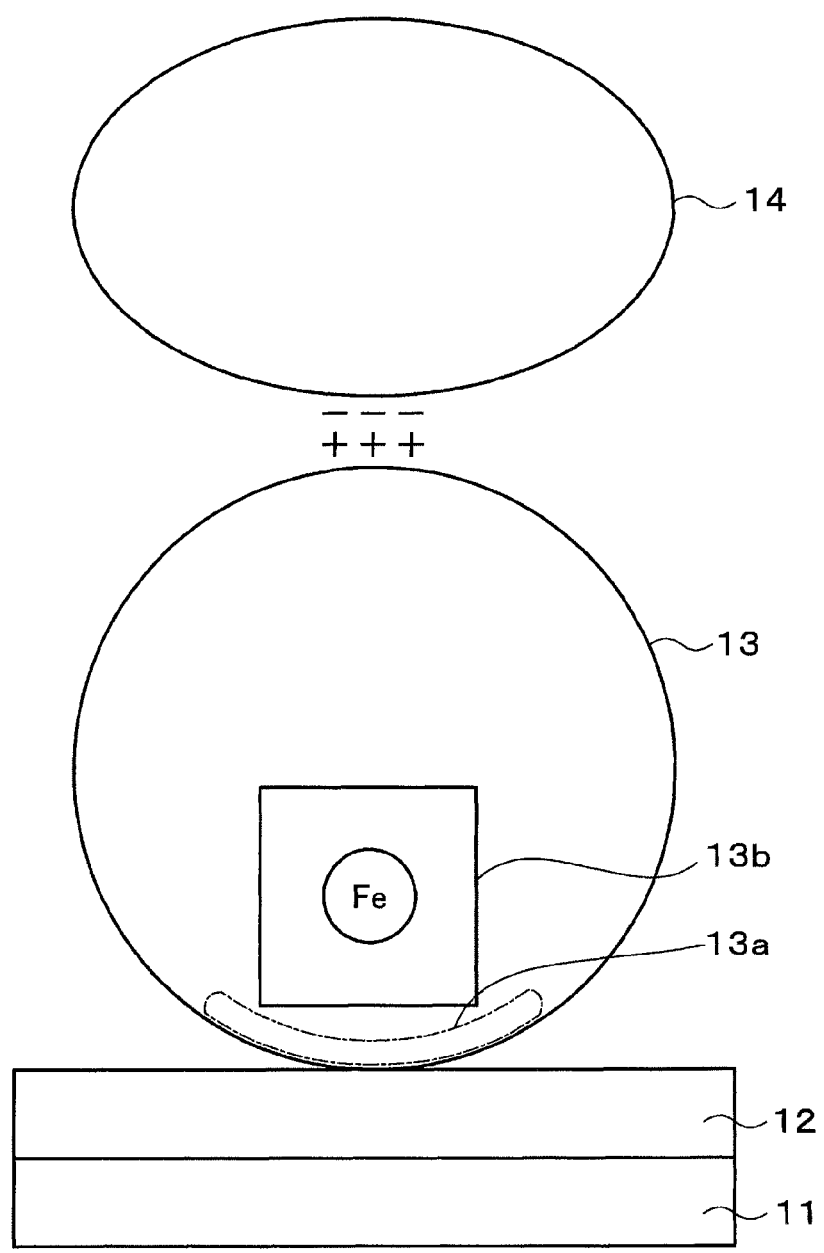
FIG. 19 is a schematic diagram illustrating the structure of a photoelectric conversion element according to a second example embodiment of the disclosure.

As illustrated in FIG. 19, a photoelectric conversion element has a protein-immobilized electrode in which the cytochrome c552 13 is immobilized to the gold electrode 11 with the self-assembled monolayer 12 in between in a manner similar to the first example embodiment. Further, a green fluorescent protein (GFP) 14 is electrostatically coupled to the cytochrome c552 13.

In the photoelectric conversion element, when light (hv) entering from the outside enters the green fluorescent protein 14, electrons in the green fluorescent protein 14 are excited. The excited electrons move to the cytochrome c552 13 and are extracted as photocurrent to the outside from the gold substrate 11. In such a manner, photoelectric conversion is performed.

The other is similar to the first example embodiment.

According to the second example embodiment, a novel photoelectric conversion element using the protein-immobilized electrode which can be stably used for long time is realized.

Although the example embodiments of the present disclosure have been described concretely above, the disclosure is not limited to the foregoing example embodiments but various modifications based on the technical idea of the disclosure are possible.

For example, the values, structures, configurations, shapes, materials, and so on described in the above example embodiments are just examples, and different values, structures, configurations, shapes, materials, and so on may be used as necessary.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A protein-immobilized electrode comprising:
a gold electrode having a self-assembled monolayer on the electrode surface, and cytochrome c552 or a derivative or variant of the cytochrome c552 immobilized on the self-assembled monolayer;
wherein the self-assembled monolayer comprises a combination of hydrophobic thiol and hydrophilic thiol, wherein the hydrophobic thiol is $HS(CH_2)_nCH_3$ and the hydrophilic thiol is $HS(CH_2)_nCH_2OH$;
wherein the content of $HS(CH_2)_nCH_2OH$ is within the range of 60 to 90% in the combination; and
wherein n is 5, 8 or 10.

2. The protein-immobilized electrode of claim 1, wherein the cytochrome c552 or its derivative or variant is immobilized in such a manner that a hydrophobic part of the cytochrome or its derivative or variant is opposed to the gold electrode side.

3. The protein-immobilized electrode of claim 1, wherein the hydrophobic thiol is $HS(CH_2)_{10}CH_3$ and the hydrophilic thiol is $HS(CH_2)_{10}CH_2OH$.

* * * * *